(12) United States Patent
Brenna et al.

(10) Patent No.: US 9,254,275 B2
(45) Date of Patent: Feb. 9, 2016

(54) BRANCHED CHAIN FATTY ACIDS FOR PREVENTION OR TREATMENT OF GASTROINTESTINAL DISORDERS

(75) Inventors: James Thomas Brenna, Ithaca, NY (US); Rinat Ran-Ressler, Ithaca, NY (US)

(73) Assignee: Cornell University, Ithaca, NY (US)

( * ) Notice: Subject to any disclaimer, the term of this patent is extended or adjusted under 35 U.S.C. 154(b) by 1054 days.

(21) Appl. No.: 12/678,465

(22) PCT Filed: Sep. 16, 2008

(86) PCT No.: PCT/US2008/076535
§ 371 (c)(1),
(2), (4) Date: May 19, 2010

(87) PCT Pub. No.: WO2009/039101
PCT Pub. Date: Mar. 26, 2009

(65) Prior Publication Data
US 2010/0298433 A1    Nov. 25, 2010

Related U.S. Application Data

(66) Substitute for application No. 60/972,992, filed on Sep. 17, 2007.

(51) Int. Cl.
| | |
|---|---|
| A61K 31/20 | (2006.01) |
| A61K 31/19 | (2006.01) |
| A23L 1/30 | (2006.01) |
| A61K 35/741 | (2015.01) |
| C12N 1/20 | (2006.01) |
| C12N 1/38 | (2006.01) |

(52) U.S. Cl.
CPC ........... *A61K 31/19* (2013.01); *A23L 1/301* (2013.01); *A23L 1/3008* (2013.01); *A23L 1/3014* (2013.01); *A61K 31/20* (2013.01); *A61K 35/741* (2013.01); *C12N 1/20* (2013.01); *C12N 1/38* (2013.01)

(58) Field of Classification Search
None
See application file for complete search history.

(56) References Cited

U.S. PATENT DOCUMENTS

| | | | |
|---|---|---|---|
| 5,112,856 A | 5/1992 | Gaginella et al. | |
| 5,411,751 A * | 5/1995 | Crissinger et al. | 426/2 |
| 5,457,194 A | 10/1995 | Luly et al. | |
| 5,541,189 A | 7/1996 | Luly et al. | |
| 5,561,140 A | 10/1996 | Kawai et al. | |
| 5,631,012 A | 5/1997 | Shanni | |
| 5,660,852 A | 8/1997 | McKeown et al. | |
| 5,776,753 A | 7/1998 | Hillman et al. | |
| 5,911,984 A | 6/1999 | Hillman et al. | |
| 5,981,590 A | 11/1999 | Panigrahi et al. | |
| 6,020,333 A | 2/2000 | Berque | |
| 6,036,992 A | 3/2000 | Borror et al. | |
| 6,080,787 A * | 6/2000 | Carlson et al. | 514/560 |
| 6,132,710 A | 10/2000 | Panigrahi et al. | |
| 6,210,890 B1 | 4/2001 | Hillman et al. | |
| 6,214,343 B1 | 4/2001 | Kink et al. | |
| 6,216,032 B1 | 4/2001 | Griffin et al. | |
| 6,251,946 B1 | 6/2001 | Vinikova et al. | |
| 6,306,908 B1 | 10/2001 | Carlson et al. | |
| 6,348,188 B1 | 2/2002 | Eccleson et al. | |
| 6,350,441 B1 | 2/2002 | Giles et al. | |
| 6,395,701 B1 | 5/2002 | Connor et al. | |
| 6,432,420 B2 | 8/2002 | Ellis et al. | |
| 6,440,439 B1 | 8/2002 | Giles et al. | |
| 6,455,716 B2 | 9/2002 | Kenneally et al. | |
| 6,518,311 B2 | 2/2003 | Kozak et al. | |
| 6,592,856 B2 | 7/2003 | Giles et al. | |
| 6,682,744 B1 | 1/2004 | Panigrahi | |
| 6,713,043 B2 | 3/2004 | Kabbash et al. | |
| 6,713,654 B1 | 3/2004 | Townsend et al. | |
| 6,804,551 B2 | 10/2004 | Griffin et al. | |
| 6,825,184 B2 | 11/2004 | Cirillo et al. | |
| 6,856,831 B2 | 2/2005 | Griffin et al. | |
| 6,890,894 B2 | 5/2005 | Connor et al. | |
| 6,903,215 B2 | 6/2005 | Batageri et al. | |
| 6,949,502 B2 | 9/2005 | Trinh et al. | |
| 7,070,965 B1 | 7/2006 | Yang | |
| 7,109,364 B2 | 9/2006 | Yang | |
| 7,129,366 B2 | 10/2006 | Yang | |
| 2007/0128266 A1 | 6/2007 | Ajani et al. | |

FOREIGN PATENT DOCUMENTS

| | | |
|---|---|---|
| CN | 1631866 A | 6/2005 |
| JP | 2007-31387 | 2/2007 |

(Continued)

OTHER PUBLICATIONS

Lin et al., Lancet, (Oct. 2006); 368(9543): 1271-83.*

(Continued)

*Primary Examiner* — Melenie McCormick
*Assistant Examiner* — Taina D Matos Negron
(74) *Attorney, Agent, or Firm* — LeClairRyan, a Professional Corporation

(57) ABSTRACT

The present invention is directed to a method of preventing or treating a gastrointestinal condition in a subject, that includes administering one or more branched chain fatty acid to the subject under conditions effective to prevent or treat the gastrointestinal condition in the subject. In general, branched chain fatty acids, in accordance with the present invention, may be non-esterified fatty acids or covalently linked to a lipid, including wax esters, sterol esters, triacylglycerols, or any other lipid-related molecular species, natural or artificial. The branched chain fatty acid can be a $C_{11}$ to $C_{26}$ branched chain fatty acid and mixtures thereof.

48 Claims, 9 Drawing Sheets

(56) References Cited

FOREIGN PATENT DOCUMENTS

| WO | WO9805221 | * | 2/1998 |
| WO | 02/100373 A1 | | 12/2002 |
| WO | 2007/046699 A2 | | 4/2007 |

OTHER PUBLICATIONS

Henry et al. Current Issues in the Management of Necrotizing Enterocolitis. 2004, vol. 28, pp. 221-233.*
Lin. Medical Hypotheses (2004), vol. 62, pp. 291-293.*
Gibson et al. Fatty Acid composition of human colostrum and mature breast milk. Am. J. of Clin. Nutrition (1981), vol. 34, pp. 252-257.*
Updegrove et al. Necrotizing enterocolitis: the evidence for use of human milk in prevention and treatment. J Hum Lact (2004), vol. 20, pp. 335-339.*
Halac et al. Prenatal and postnatal corticosteroid therapy to prevent neonatal necrotizing enterocolitis: a controlled trial.J. Pediatr (1990), vol. 117, pp. 132-138.*
Alonso et al. Fatty Acid Composition of Caprine Milk: Major, Branched-Chain, and Trans Fatty Acids. (J. Dairy Sci. (1999), vol. 82, pp. 878-884).*
Baumgart et al. Inflammatory bowel disease: cause and immunobiology. (Lancet (2007) vol. 369, pp. 1627-1640).*
Kanno. Emulsifying Properties of Bovine Milk Fat Globule Membrane in Milk Fat Emulsion: Conditions for the Reconstitution of Milk Fat GLobules. Journal of Food Science (1989), vol. 54, pp. 1534-1539.*
Smith et al. Role of Helicobacter pylori Gastritis in Gastric Atrophy, Intestinal Metaplasia, and Gastric Neoplasia. (2000) vol. 48, pp. 313-320.*
Stoutenbeek, et al. "The Effect of Selective Decontamination of the Digestive Tract on Colonisation and Infection Rate in Multiple Trauma Patients", Intensive Care Med. 10:185-192 (1984).
Gibson, et al. "Dietary Modulation of the Human Colonic Microbiota: Introducing The Concept of Prebiotics", Journal of Nutrition 125:1401-1412 (1995).
PCT International Search Report and Written Opinion PCT/US2008/076535 Sep. 16, 2008.
Tollin et al., "Vernix Caseosa as a Multi-Component Defence System Based on Polypeptides, Lipids and their Interactions," Cell. Mol. Life Sci. 62:2390-99 (2005).
Vanderhoof et al., "Current and Potential Uses of Probiotics," Ann. Allergy Asthma Immunol. 93(5 Suppl 3):S33-37 (2004).
Ran-Ressler et al., "Comparative Branched Chain Fatty Acid Concentrations in Vernix and Meconium of Human Infants," Abstract 684.4, The FASEB Journal 21(5):A701 (Apr. 2007).
Christiansen et al., "Randomized, Controlled Trial of Slow Versus Rapid Feeding Volume Advancement in Preterm Infants," J. Pediatrics 146(5):710-711 (2005).
Rissmann et al., "New Insights Into Ultrastructure, Lipid Composition and Organization of Vernix Caseosa," J. Investigative Dermatology 126(8):1823-1833 (2006).
Ran-Ressler et al., "Branched Chain Fatty Acids are Constituents of the Normal Healthy Newborn Gastrointestinal Tract," Pediatric Res. 64(6):605-609 (2008).
Ran-Ressler et al., "Comparative Branched Chain Fatty Acid Concentrations in Vernix and Meconium of Human Infants," Poster Presentation, Experimental Biology Annual Meeting 2007, Washington, DC, Apr. 28-May 2, 2007.
European Search Report for Corresponding EP Application No. 08831860.5 (mailed Apr. 11, 2011).
European Examination Report for Corresponding EP Application No. 08831860.5 (mailed Jan. 10, 2013).
First Office Action for Corresponding China Application No. 2008801073801 (mailed Oct. 10, 2012).
Second Office Action for Corresponding China Application 2008801073801 (mailed Aug. 26, 2013).
Net Doctor, Unguentum M. Cream (http://www.netdoctor.co.uk/skin-and-hair/medicines/unguentum-m-cream.html) (last updated Aug. 20, 2011).
Ballance et al., "Pathology of Neonatal Necrotizing Entercolitis: A Ten-Year Experience," J. Pediatr. 117(1 Pt. 2):S6-13 (1990).
Braat et al., "Interleukin-10-Based Therapy for Inflammatory Bowel Disease," Expert Opin. Biol. Ther. 3(5):725-731 (2003).
Hofmann et al., "Biological Properties and Regulation of IL-10 Related Cytokines and Their Contribution to Autoimmune Disease and Tissue Injury," Clinical Immunology 143:116-127 (2012).
Hommes & van Deventer, "Anti- and Proinflammatory Cytokines in the Pathogenesis of Tissue Damage in Crohn's Disease," Curr. Opin. Clin. Nutr. Metab. Care 3:191-195 (2000).
Li & He, "IL-10 and Its Related Cytokines for Treatment of Inflammatory Bowel Disease," World J. Gastroenterol. 10 (5):620-625 (2004).
Lindsay & Hodgson, "Review Article: The Immunoregulatory Cytokine Interleukin-10—a Therapy for Crohn's Disease," Aliment Pharmacol. Ther. 15:1709-1716 (2001).
Ouyang et al., "Regulation and Functions of the IL-10 Family of Cytokines in Inflammation and Disease," Annu. Rev. Immunol. 29:71-109 (2011).
Rennick & Fort, "Lessons From Genetically Engineered Animal Models XII. IL-10-Deficient (IL-10-/-) Mice and Intestinal Inflammation," Am. J. Physiol. Gastrointest. Liver Physiol. 278:G829-G833 (2000).

* cited by examiner

BRANCHED CHAIN FATTY ACIDS FOR PREVENTION OR TREATMENT OF GASTROINTESTINAL DISORDERS

This application claims the benefit of U.S. Provisional Patent Application Ser. No. 60/972,992, filed Sep. 17, 2007, which is hereby incorporated by reference in its entirety.

The subject matter of this application was made with support from the United States Government under National Institutes of Health (NIH) Grant No. GM071534. The U.S. government has certain rights.

FIELD OF THE INVENTION

The present invention is directed to methods for prevention or treatment of gastrointestinal disorders.

BACKGROUND OF THE INVENTION

Branched chain fatty acids (BCFA) are mostly saturated fatty acids (SFA) with one or more methyl branches on the carbon chain. BCFA are synthesized mainly by the skin and have long been known to be a major component of vernix caseosa (10-20% dry weight) (Nicolaides et al, "Skin Lipids. 3. Fatty Chains in Skin Lipids. The Use of Vernix Caseosa to Differentiate between Endogenous and Exogenous Components in Human Skin Surface Lipid," *J Am Oil Chem Soc* 42:702-707 (1965)). Among terrestrial animals, vernix is unique to humans, and is not found in other land mammals, including other primates (Pickens et al., "Characterization of Vernix Caseosa: Water Content, Morphology, and Elemental Analysis," *J Invest Dermatol* 115:875-881 (2000)). Vernix is made of sebum and fetal corneocytes (Nicolaides et al., "Skin Lipids. 3. Fatty Chains in Skin Lipids. The Use of Vernix Caseosa to Differentiate between Endogenous and Exogenous Components in Human Skin Surface Lipid," *J Am Oil Chem Soc* 42:702-707 (1965) and Narendran et al., "Interaction between Pulmonary Surfactant and Vernix: A Potential Mechanism for Induction of Amniotic Fluid Turbidity," *Pediatr Res* 48:120-124 (2000)) and is produced by fetal skin starting at 24 weeks gestational age and continuing until term birth (Moore et al., "Fetal Cocaine Exposure: Analysis of Vernix Caseosa," *J Anal Toxicol* 20:509-511 (1996)). During the third trimester vernix sloughs off as particulates that become suspended in amniotic fluid (Narendran et al., "Interaction between Pulmonary Surfactant and Vernix: A Potential Mechanism for Induction of Amniotic Fluid Turbidity," *Pediatr Res* 48:120-124 (2000) and Yoshio et al., "Antimicrobial Polypeptides of Human Vernix Caseosa and Amniotic Fluid: Implications for Newborn Innate Defense," *Pediatr Res* 53:211-216 (2003)), possibly aided by lung surfactant phospholipids that also enter the amniotic fluid. The fetus normally swallows amniotic fluid in amounts approaching 500 ml at the end of gestation (Miettinen et al., "Gas-liquid Chromatographic and Mass Spectrometric Studies on Sterols in Vernix Caseosa, Amniotic Fluid and Meconium," *Acta Chem Scand* 22:2603-2612 (1968) and Sherman et al., "Fetal Swallowing: Correlation of Electromyography and Esophageal Fluid Flow," *Am J Physiol* 258:R1386-1394 (1990)) and with it vernix. Thus, the late term fetal gut is normally exposed to vernix and its BCFA, increasingly so as parturition approaches.

Vernix dry matter is composed of approximately equal amounts of protein and lipids (Pickens et al., "Characterization of Vernix Caseosa: Water Content, Morphology, and Elemental Analysis," *J Invest Dermatol* 115:875-881 (2000) and Hoeger et al., "Epidermal Barrier Lipids in Human Vernix Caseosa: Corresponding Ceramide Pattern in Vernix and Fetal Skin," *Br J Dermatol* 146:194-201 (2002)). Lipid fractions in vernix have been comprehensively characterized (Nicolaides et al., "The Fatty Acids of Wax Esters and Sterol Esters from Vernix Caseosa and from Human Skin Surface Lipid," *Lipids* 7:506-517 (1972); Rissmann et al., "New Insights into Ultrastructure, Lipid Composition and Organization of Vernix Caseosa," *J Invest Dermatol* 126:1823-1833 (2006) and Kaerkkaeinen et al., "Lipids of Vernix Caseosa," *J Invest Dermatol* 44:333-338 (1965)) and shown to be 25-30% sterol esters (SE), 18-36% triglycerides (TAG), 12-16% wax esters (WE), 9% squalene, 5% ceramides, and low levels of non-esterified fatty acid (NEFA) fraction was also detected by some (Rissmann et al., "New Insights into Ultrastructure, Lipid Composition and Organization of Vernix Caseosa," *J Invest Dermatol* 126:1823-1833 (2006) and Tollin et al., "Vernix Caseosa as a Multi-component Defence System Based on Polypeptides, Lipids and Their Interactions," *Cell Mol Life Sci* 62:2390-2399 (2005)) but not by others (Nazzaro-Porro et al., "Effects of Aging on Fatty Acids in Skin Surface Lipids," *J Invest Dermatol* 73:112-117 (1979)). BCFA are found in all acyl-carrying lipid classes, WE (16-53%) and SE (27-62%) (Nicolaides et al., "The Fatty Acids of Wax Esters and Sterol Esters from Vernix Caseosa and from Human Skin Surface Lipid," *Lipids* 7:506-517 (1972); Rissmann et al., "New Insights into Ultrastructure, Lipid Composition and Organization of Vernix Caseosa," *J Invest Dermatol* 126:1823-1833 (2006); Kaerkkaeinen et al., "Lipids of Vernix Caseosa," *J Invest Dermatol* 44:333-338 (1965) and Nazzaro-Porro et al., "Effects of Aging on Fatty Acids in Skin Surface Lipids," *J Invest Dermatol* 73:112-117 (1979)), as well as in the TAG (18-21%) and NEFA (21%) fractions (Rissmann et al., "New Insights into Ultrastructure, Lipid Composition and Organization of Vernix Caseosa," *J Invest Dermatol* 126:1823-1833 (2006)).

Apart from skin (Nicolaides et al., "Skin Lipids. 3. Fatty Chains in Skin Lipids. The Use of Vernix Caseosa to Differentiate between Endogenous and Exogenous Components in Human Skin Surface Lipid," *J Am Oil Chem Soc* 42:702-707 (1965); Nicolaides et al., "The Fatty Acids of Wax Esters and Sterol Esters from Vernix Caseosa and from Human Skin Surface Lipid," *Lipids* 7:506-517 (1972) and Nicolaides et al., "Skin Lipids: Their Biochemical Uniqueness," *Science* 186:19-26 (1974)), BCFA are at very low levels in internal tissue (Nicolaides et al., "Skin Lipids: Their Biochemical Uniqueness," *Science* 186:19-26 (1974)), but are also found in human milk (Jensen et al., "Handbook of Milk Composition," *Academic Press Inc.*, San Diego, (1995); Egge et al., "Minor Constituents of Human Milk. IV. Analysis of the Branched Chain Fatty Acids," *Chem Phys Lipids* 8:42-55 (1972) and Gibson et al., "Fatty Acid Composition of Human Colostrum and Mature Breast Milk," *Am J Clin Nutr* 34:252-257 (1981)) at concentrations as high as 1.5% w/w of total fatty acids (FA). This level is comparable to and in some cases greater than that of docosahexaenoic acid (DHA, 22:6n-3) and arachidonic acid (ARA, 20:4n-6) in the same milk. For instance, a 1981 publication reported the concentration of anteiso 17:0 in Australian women's colostrum to be 0.45% w/w of total FA, exceeding the concentrations of DHA (0.32% w/w) and ARA (0.4% w/w) (Gibson et al., "Fatty Acid Composition of Human Colostrum and Mature Breast Milk," *Am J Clin Nutr* 34:252-257 (1981)).

Meconium, the newborn's first fecal pass, first appears in the fetal GI tract at around 12 weeks of gestational age, and is normally passed after birth (Ahanya et al., "Meconium Passage In Utero: Mechanisms, Consequences, and Management," *Obstet Gynecol Surv* 60:45-56 (2005); Gareri et al., "Drugs of Abuse Testing in Meconium," *Clin Chim Acta* 366:101-111 (2006); and Ostrea et al., "Fatty Acid Ethyl Esters in Meconium: Are They Biomarkers of Fetal Alcohol Exposure and Effect?" *Alcohol Clin Exp Res* 30:1152-1159 (2006)). It consists of amniotic fluid residue, skin and gastrointestinal (GI) epithelial cells, GI secretions and enzymes, lipids, sugars, proteins, cholesterol, sterols, bile acid and salts (Ahanya et al., "Meconium Passage In Utero: Mechanisms, Consequences, and Management," *Obstet Gynecol Surv* 60:45-56 (2005); Gareri et al., "Drugs of Abuse Testing in Meconium," *Clin Chim Acta* 366:101-111 (2006); Buchanan et al., "Chemical Comparison of Normal Meconium and Meconium from a Patient with Meconium Ileus," *Pediatrics* 9:304-310 (1952); and Righetti et al., "Proton Nuclear Magnetic Resonance Analysis of Meconium Composition in Newborns," *J Pediatr Gastroenterol Nutr* 36:498-501 (2003)). Meconium contains 12% dry weight lipid (Buchanan et al., "Chemical Comparison of Normal Meconium and Meconium from a Patient with Meconium Ileus," *Pediatrics* 9:304-310 (1952)), and there is only one unconfirmed study reporting BCFA in meconium (Terasaka et al., "Free Fatty Acids of Human Meconium," *Biol Neonate* 50:16-20 (1986)). There are no studies linking BCFA composition of vernix and meconium in the same infants.

It was hypothesized that vernix BCFA of term newborns would survive the alimentary canal and be found in meconium. The test of this hypothesis led to characterizing the relative BCFA profiles of vernix and meconium to establish the degree to which the profile is altered by the sterile fetal gut in utero.

The present invention is directed to overcoming the deficiencies in the art.

SUMMARY OF THE INVENTION

A first aspect of the present invention relates to a method of preventing or treating a gastrointestinal condition in a subject that includes administering one or more branched chain fatty acid to the subject under conditions effective to prevent or treat the gastrointestinal condition in the subject.

A second aspect of the present invention relates to a method of promoting gastrointestinal health in a subject that includes administering one or more branched chain fatty acid to the subject under conditions effective to promote gastrointestinal health in the subject.

A third aspect of the present invention relates to a method of promoting propagation of probiotic organisms that includes providing a population of cells comprising probiotic organisms and administering one or more branched chain fatty acid to the population of cells under conditions effective to promote propagation of probiotic organisms in the population of cells.

A fourth aspect of the present invention relates to a formulation which includes one or more branched chain fatty acid and an aqueous phase emulsified with the one or more branched chain fatty acid, where the formulation includes over 25 wt % of the one or more branched chain fatty acid.

Vernix suspended in amniotic fluid is normally swallowed by the late term fetus. It was hypothesized that branched chain fatty acids (BCFA), long known to be major vernix components, would be found in meconium and that the profiles would differ systematically. Vernix and meconium were collected from term newborns and analyzed. BCFA-containing lipids constituted about 12% of vernix dry weight, and were predominantly saturated, and had 11 to 26 carbons per BCFA. In contrast, meconium BCFA had 16 to 26 carbons, and were about 1% of dry weight. Meconium BCFA were mostly in the iso configuration, whereas vernix BCFA contained dimethyl and middle chain branching, and five anteiso BCFA. The mass of BCFA entering the fetal gut as swallowed vernix particles is estimated to be 180 mg in the last month of gestation while the total mass of BCFA found in meconium is estimated to be 16 mg, thus most BCFA disappear from the fetal gut. The BCFA profiles of vernix and meconium show that BCFA are major components of normal healthy term newborn gastrointestinal tract. BCFA are candidates for agents that play a role in gut colonization and should be considered a nutritional component for the fetus/newborn.

BRIEF DESCRIPTION OF THE DRAWINGS

FIGS. 5A and 5C are scaled to match for n-16:0 and the 18:1 isomers for convenient visual comparison of relative abundances. FIG. 5A shows control Caco-2 cells showing no significant BCFA. FIG. 5B shows a mixture of pure BCFA (iso-14:0, anteiso-17:0, iso-18:0, iso-20:0). FIG. 5C shows total FA from BCFA-treated BCFA in FIG. 5B. iso-16:0 is detected as a novel product bio-synthesized by the cells, most likely to be derived from iso-14:0 from chain elongation. RIC are reconstructed from full mass spectra collected each one second, positively identifying the structural assignments.

FIG. 6A shows RIC of native (untreated) cells. FIG. 6B shows RIC of BCFA treated cells. FIG. 6C shows a selected ion chromatogram showing elution of 16:0's. FIG. 6D shows the mass spectrum of the first peak in FIG. 6B, characteristic of newly synthesized iso-16:0. FIG. 6E shows the mass spectrum of n-16:0, normally present in cells, with negligible m/z 255 peak (loss of methyl).

Figure 9:
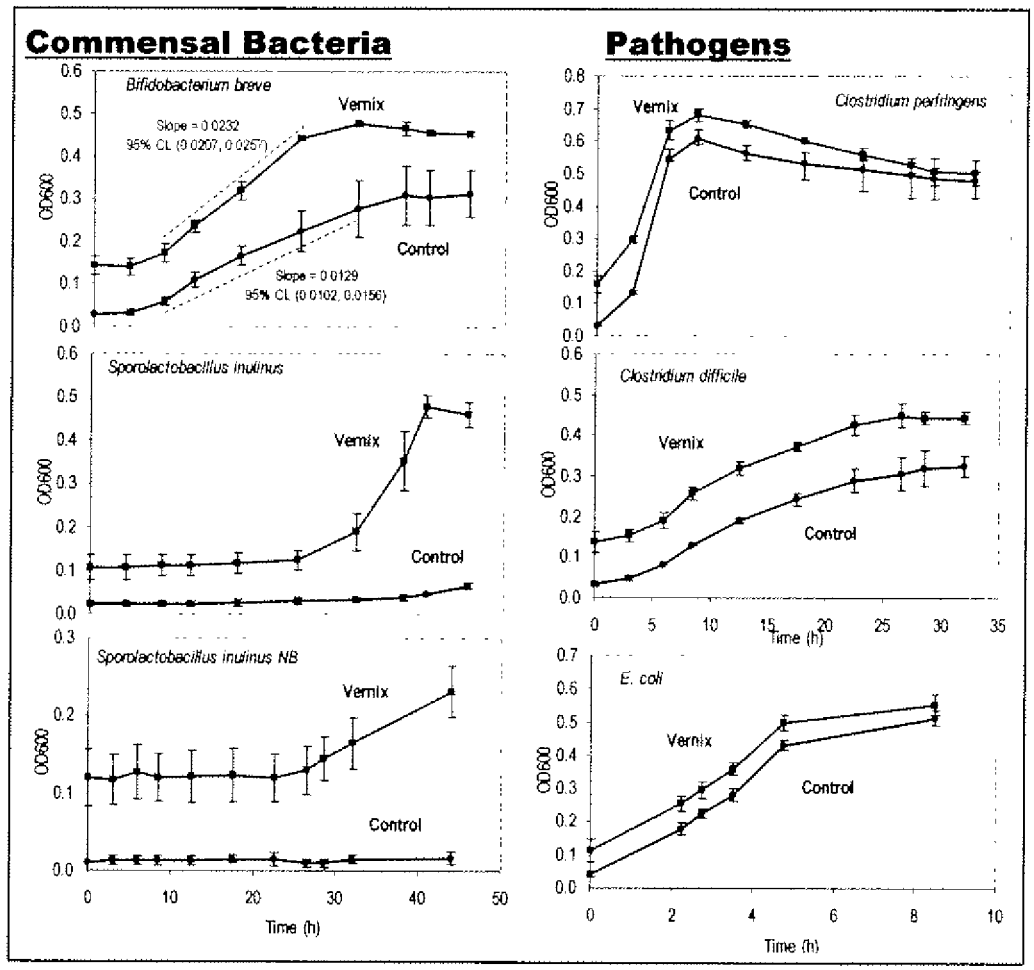

FIG. 9 shows *B. breve* (TSB) or *S. inulinus* (TSB or NB) growth is enhanced with vernix compared to a control. Pathogen growth was not affected by vernix. The higher offset for the vernix curves is due to undissolved particulates in vernix.

DETAILED DESCRIPTION OF THE INVENTION

One aspect of the present invention relates to a method of preventing or treating a gastrointestinal condition in a subject that includes administering one or more branched chain fatty acid to the subject under conditions effective to prevent or treat the gastrointestinal condition in the subject.

A second aspect of the present invention relates to a method of promoting gastrointestinal health in a subject that includes administering one or more branched chain fatty acid to the subject under conditions effective to promote gastrointestinal health in the subject.

For each method, a subject in need may be selected. The method of preventing or treating a gastrointestinal condition in a subject may be carried out in a human, in particular, in a fetus, infant, newborn infant, child, or an adult.

The gastrointestinal condition can be mediated by infection of the subject's gastrointestinal tract by a pathogenic bacteria (e.g., necrotizing enterocolitis) or may require microbial colonization of the subject's gastrointestinal tract (e.g., in conjunction with an antibiotic treatment). The gastrointestinal condition may also be a disease of the intestine involving inflammation, such as inflammatory bowel disease.

In general, branched chain fatty acids, in accordance with the present invention, may be non-esterified fatty acids or covalently linked to a lipid, including wax esters, sterol esters, triacylglycerols, or any other lipid-related molecular species, natural or artificial.

The branched chain fatty acid can be a $C_{11}$ to $C_{26}$ branched chain fatty acid and mixtures thereof. The branched chain fatty acid may be 4,7-dimethyl-nonanoic acid, 4,8-dimethyl-decanoic acid, 8-methyl-undecanoic acid, iso-dodecanoic acid, 4,8-dimethyl-undecanoic acid, 4,9-dimethyl-undecanoic acid, iso-tridecanoic acid, anteiso-tridecanoic acid, 4,10-dimethyl-dodecanoic acid, iso-tetradecanoic acid, 4,11-dimethyl-tridecanoic acid, iso-pentadecanoic acid, anteiso-pentadecanoic acid, 8,10-dimethyl-tetradecanoic acid, 4,12-dimethyl-tetradecanoic acid, iso-hexadecanoic acid, 2-methyl hexadecanoic acid, 4,11-dimethyl-pentadecanoic acid, 4,13-dimethyl-pentadecanoic acid, iso-heptadecanoic acid, anteiso heptadecanoic acid, iso-octadecanoic acid, iso-eicosanoic acid, anteiso-heneicosanoic acid, iso-dodecanoic acid, iso-tetracosanoic acid, iso-pentacosanoic acid, anteiso-pentacosanoic acid, iso-hexacosanoic acid, phytanic acid, pristanic acid, or mixtures thereof.

The branched chain fatty acid may also be saturated and monounsaturated fatty acids or mixtures thereof.

Further, the branched chain fatty acid can be a branched form of a fatty acid such as an octanoic acid, a decanoic acid, a lauric acid, a myristic acid, a palmitic acid, a stearic acid, an eicosanoic acid, a palmitoliec acid, an oleic acid, or mixtures thereof.

The therapeutic agent, regardless of its mode of action, can be administered to a patient in the form of a pharmaceutical composition that also includes a pharmaceutically-acceptable carrier. The pharmaceutical composition may be in a liquid or solid dosage form including, but not limited to, tablets, capsules, powders, solutions, suspensions, or emulsions.

The therapeutic agent of the present invention, and thus the pharmaceutical compositions of the present invention, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, by application to mucous membranes (such as, that of the nose, throat, and bronchial tubes), or by introduction into one or more lymph nodes.

In addition to being used in pharmaceutical compositions, branched chain fatty acids, in accordance with the present invention, can be added to any of a variety of food products, including milk, infant formula, baby food, dietary supplements, vegetable oils, mayonnaise and condiments, yogurt, margarine and spreads, shortenings, and any food that includes fat or can be formulated with fat.

A third aspect of the present invention relates to a method of promoting propagation of probiotic organisms that includes providing a population of cells comprising probiotic organisms and administering one or more branched chain fatty acid to the population of cells under conditions effective to promote propagation of probiotic organisms in the population of cells.

The method of promoting propagation of probiotic organisms may be carried out in vitro or in vivo.

The probiotic organism may be selected from the group consisting of *Lactobacillus* species, *Bifidobacterium* species, other lactic acid bacteria, and nonlactic acid bacteria, and mixtures thereof.

The probiotic organism may be a *Lactobacillus* species, such as *L. acidophilus, L. amylovorus, L. brevis, L. casei, L. casei* subsp. *rhamnosus* (*Lactobacillus* GG), *L. caucasicus, L. crispatus, L. delhrueckii* subsp. *bulgaricus* (*L. bulgaricus*), *L. fermentum* (*L. fermenti*), *L. gasseri, L. helveticus, L. johnsonii, L. lactis, L. leichmannii, L, paracasei, L. plantarum, L. reuteri, L, rhamnosus* or mixtures thereof.

The probiotic organism may be a *Bifidobacterium* species, such as *B. adolescentis, B. bifidum, B. breve, B. infantis, B. lactis* (*B. animalis*), *B. licheniformis, B. longum* or mixtures thereof.

The probiotic organism may be a lactic acid bacteria, such as *Enterococcus faecium, Lactococcus lactis, Leuconstoc mesenteroides, Pediococcus acidilactici, Streptococcus thermophilus*, or mixtures thereof.

The probiotic organism may be a nonlactic acid bacteria, such as *Bacillus subtilis, Escherichia coli* strain nissle, *Saccharomyces boulardii, Saccharomyces cerevisiae* or mixtures thereof.

To the extent, the method of propagating probiotic organisms is carried out in subjects, it is formulated and administered in substantially the same manner as noted above.

Probiotics have proven effective in NEC (necrotizing enterocolitis) trials, specifically combinations of *Lactobacillus acidophilus* and *Bifidobacterium infantis* (Hoyos A B., "Reduced Incidence of Necrotizing Enterocolitis Associated with Enteral Administration of *Lactobacillus acidophilus* and *Bifidobacterium infantis* to Neonates in an Intensive Care Unit," *Int J Infect Dis* 3:197-202 (1999) and Lin et al., "Oral Probiotics Reduce the Incidence and Severity of Necrotizing Enterocolitis in Very Low Birth Weight Infants," *Pediatrics* 115:1-4 (2005), which are hereby incorporated by reference in their entirety) or Bifidobacteria *infantis, Streptococcus thermophilus*, and Bifidobacteria *bifidus* (Bin-Nun et al., "Oral Probiotics Prevent Necrotizing Enterocolitis in Very Low Birth Weight Neonates," *J Pediatr* 147:192-6 (2005), which is hereby incorporated by reference in its entirety).

Probiotic bacteria are sold mainly in fermented foods and dairy products, specifically, yogurt-like products form the largest segment of the market for probiotic products (Heller et al., "Probiotic Bacteria in Fermented Foods: Product Characteristics and Starter Organisms," *Am J Clin Nutr* 73(suppl): 374S-9S (2001), which is hereby incorporated by reference in its entirety). As used herein, "probiotics" are defined as viable microorganisms, sufficient amounts of which reach the intestine in an active state and thus exert positive health effects (de Vrese et al., "Probiotics, Prebiotics, and Synbiotics," *Adv Biochem Eng Biotechnol* 111:1-66 (2008), which is hereby incorporated by reference in its entirety).

A fourth aspect of the present invention relates to a formulation which includes one or more branched chain fatty acid and an aqueous phase emulsified with the one or more branched chain fatty acid, where the formulation includes over 25 wt % of the one or more branched chain fatty acid.

The formulation may include up to 98 wt %, preferably up to 70 wt %, of the branched chain fatty acid or a mixture thereof. In addition, the branched chain fatty acid or a mixture thereof of the formulation may include up to 20 wt % of isomyristic acid, isopentadecoanoic acid, anteisopentadecanoic acid, isopalmitic acid, isoeicosanoic acid, anteisoeicosanoic acid, isodocosanoic acid, isotetracosanoic acid, isohexacosanoic acid or combinations thereof. The formulation may also include an emulsifier.

Vernix has 29% BCFA, meconium is about 12%, and breastmilk is about 1%. Vernix and meconium are present in the fetus and the immediate newborn, while breastmilk applies after birth. The formulation of the present invention is designed to achieve enhanced results compared to vernix. It is advantageous for the BCFA to be emulsified in a water (aqueous) phase. Such an emulsion does not correspond to anything found in vernix or meconium, or breastmilk. A suitable BCFA formulation for prevention or treatment of abnormal bacterial flora in the gastrointestinal (GI) tract, and for optimization of intestinal health, would be a mixture of fat and aqueous solution of up to 50% fat. The aqueous phase includes any solution compatible with the GI tract. The mixture should be emulsified with any food grade emulsifier acceptable for pediatric use, such as soy lecithin.

EXAMPLES

The following examples are provided to illustrate embodiments of the present invention but are by no means intended to limit its scope.

Materials and Methods for Examples 1-5

Sample Collection

Eighteen samples of vernix and meconium were collected from 18 normal term newborns at Cayuga Medical Center in Ithaca, N.Y. Vernix was removed from the shoulder regions in the birthing room, placed in clean tubes and stored at −80° C. until analysis. Meconium was collected from diapers and similarly transferred into clean tubes and stored at −80° C. until analysis.

FA Analysis

Total lipids were extracted from the vernix and the meconium samples according to a modified Bligh and Dyer method (Bligh et al., "A Rapid Method of Total Lipid Extraction and Purification," *Can J Biochem Physiol* 37:911-917 (1959), which is hereby incorporated by reference in its entirety). Fatty acids are overwhelmingly found in mammalian pools, such as vernix and meconium, as acyl moieties which are constituents of higher molecular weight lipid molecules such as TAG, SE, and WE. For detailed molecular analysis, fatty acyl groups are hydrolyzed and fatty acid methyl esters (FAME) synthesized for analysis. FAME were prepared using 14% BF3 in methanol (Sigma Chemical, St. Louis, Mo.). Butylated hydroxytoluene (BHT) was added to methanol as an antioxidant. Heptadecanoic acid (Sigma Chemical, St Louis, Mo.) in chloroform was used as an internal standard. This routine step obscures heptadecanoic acid which is normally rare in mammalian tissue but is present in vernix and meconium. Because of the extraordinary diversity of FA in these samples, any internal standard interferes with analysis of one or more FA in some of the samples. A correction was applied to estimate the extent of interference, and the signals were carefully calibrated against external standards.

FAME analyses were performed using a Hewlett Packard 5890 series H gas chromatograph (GC). A BPX-70 column (60 m×0.32 mm×0.25 μm, SGE, Austin, Tex.) was used for the analysis with $H_2$ as the carrier gas. FAME identities were determined by a chemical ionization (CI) and electron impact (EI) mass spectrometry (MS), using a Varian Star 3400 GC coupled to a Varian Saturn 2000 ion trap MS. BCFA FAME identities were based on GC retention time of each substance and its electron impact mass spectra. FAME mass spectral assignments were confirmed by conversion of the FAME to picolinyl ester derivatives according to the method described by Yang et al. (Yang et al., "Picolinyl Ester Fragmentation Mechanism Studies with Application to the Identification of Acylcarnitine Acyl Groups Following Transesterification," *J Am Soc Mass Spectrom* 17:1620-1628 (2006), which is hereby incorporated by reference in its entirety), followed by GC/MS analysis and comparison to literature spectra (Carballeira et al., "Characterization of Novel Methyl-branched Chain Fatty Acids from a Halophilic *Bacillus* Species," *J Nat Prod* 64:256-259 (2001); Suutari et al., "Signature GLC-MS Ions in Identification of Delta 5 and Delta 9 Unsaturated Iso and Anteiso Branched Chain Fatty Acids," *J Microbiol Methods* 17:39-48 (1993); Karlsson et al., "Studies on Feather Waxes of Birds," *Arkiv for Kemi* 31:143-158 (1969); Yu et al., "Location of Methyl Branchings in Fatty Acids: Fatty Acids in Uropygial Secretion of Shanghai Duck by GC-MS of 4,4-Dimethyloxazoline Derivatives," *Lipids* 23:804-810 (1988); Apon et al., "The Determination of the Position Isomers of the Methyl Branches Fatty Acids Methyl Esters by Capillary GC/MS," *J Chromatogr Sci* 13:467-473 (1975); and Harvey et al., "Identification of Long-chain Fatty Acids and Alcohols from Human Cerumen by the Use of Picolinyl and Nicotinate Esters," *Biomed Environ Mass Spectrom* 18:719-723 (1989), which are hereby incorporated by reference in their entirety).

An equal weight FAME mixture (68A; Nuchek Prep, Elysian, Minn.) was used to calculate response factors. The following were also used as standards: n-11:0 up to n-24:0 (Nuchek Prep, Elysian, Minn.); iso 13:0, anteiso 13:0, iso 15:0, anteiso 15:0; iso 17:0, anteiso 17:0 (Larodan Fine Chemicals AB, Malmo, Sweden) and 10 methyl hexadecanoic acid (Matreya LLC, Pleasant Gap, Pa.). FA levels were expressed as weight % of total fatty acids for all 11 to 32 carbons FA.

Statistics

Data are expressed as mean±SD for study population characteristics, and as mean±SEM for FA analysis. Statistical analyses were made using JMP 6 (SAS Institute, Cary, N.C.). Differences in mean of each FA were calculated using one sample t-test for non-zero differences, with $p<0.05$ declared significant.

Subjects

Characteristics of the study population are presented in Table 1. No complications were present for any of the newborns other than as noted. All but two newborns were by vaginal delivery. Six mothers received antibiotic treatment during pregnancy; five of them gave birth to female infants.

TABLE 1

Characteristics of study population (mean ± SD (range)).

| | |
|---|---|
| Mother's age (years) | 29 ± 5.8   18-42 |
| Gestational age (weeks) | 40 ± 1   38-41 |
| Birthweight (kg) | 3.3 ± 0.5   2.3-4.4 |
| Gender | 10 female, 8 males |
| Delivery | 16 vaginal, 2 CS* |
| Antibiotics | 5 female, 1 male |

*Cesarian section

Example 1

Overall FA Distribution

A profile of FA classes is shown in Table 2. Comparisons of all classes were significant at the p<0.05 level. BCFA constituted almost a third (29.1±1.5% w/w) of all FA in vernix and were significantly higher compared to the mean levels in meconium (17.5±1.3% w/w; p<0.05). This drop in BCFA was accompanied by a reciprocal increase in normal (n-) saturated FA (n-SFA) specifically, 34±1.9% w/w in vernix and 51.3±3.0% w/w in meconium (p<0.05). Differences in n-monounsaturated fatty acids (MUFA) and polyunsaturated fatty acid (PUFA) were modest by comparison.

TABLE 2

Profile of FA classes (% w/w) in vernix and meconium (mean ± SEM)

| FA | Vernix | Meconium |
|---|---|---|
| BCFA | 29.1 ± 1.5* | 17.5 ± 1.3 |
| n-SFA | 34 ± 1.9* | 51.3 ± 3.0 |
| n-MUFA | 31.0 ± 1.7* | 22.4 ± 2.1 |
| PUFA | 3.9 ± 0.4* | 7.1 ± 1.1 |

*p < 0.05

Overall, BCFA hydrolyzed from their native lipid classes constituted 5.8% of dry weight of vernix, corresponding to approximately 12% of dry weight of vernix within the native BCFA-containing lipids. Meconium had 0.55% dry weight of hydrolyzed BCFA and an estimated 1% of BCFA-containing lipids.

Example 2

BCFA Distribution in Vernix and Meconium

Figure 1:
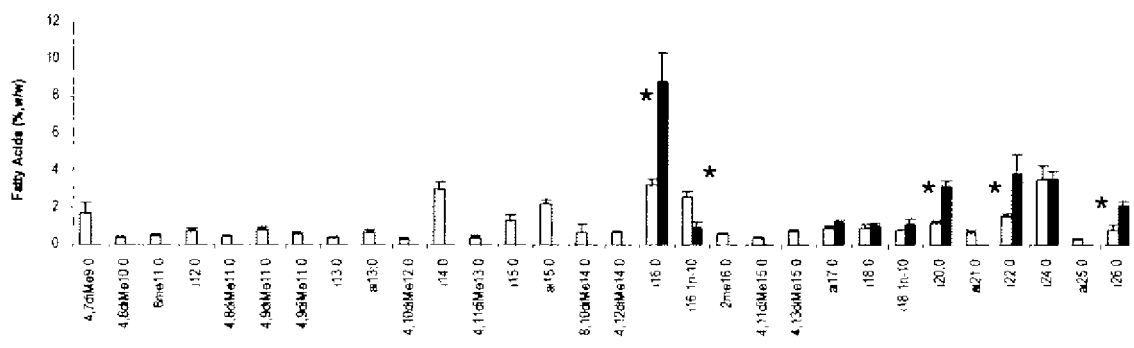
FIG. 1 shows BCFA methyl esters profiles for vernix and meconium (means±SEM, n≤18 newborn) listed left to right in order of molecular weight. Means are for those FA appearing in samples from at least three newborns. iso-BCFA have a dimethyl terminal structure: iso-16:0 is synonymous with 14-methyl-15:0 (14-methyl-pentadecanoic acid). anteiso-BCFA have a methyl branch at the n-2 position: anteiso-17:0 is synonymous with 14-methyl-16:0 (14-methyl-hexadecanoic acid). i-iso; ai=anteiso; Me=methyl; diMe=two methyl branches. Key: ☐ vernix; ■ meconium. *p<0.05

FIG. 1 is a graphical summary of the BCFA profiles for vernix and meconium for those BCFA detected in samples from at least 3 newborns, presented left to right in order of carbon number. In total, 30 BCFA were identified in vernix while nine were also detected in meconium. Vernix BCFA ranged from 11 to 26 carbon atoms and were primarily saturated apart from two iso monounsaturates. iso BCFA, anteiso BCFA, middle chain monomethyl BCFA and dimethyl BCFA were all detected among vernix BCFA. In contrast, meconium BCFA had a much more restricted range of carbon numbers, from 16 to 26 carbons. Of the nine meconium BCFA, eight were iso BCFA, of which two were MUFA, and one was anteiso.

Example 3

Profile of the iso BCFA in Vernix and Meconium

Figure 2:
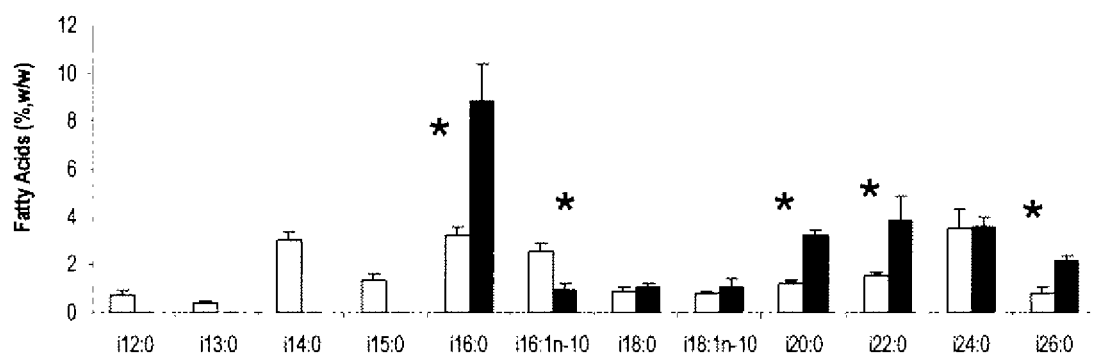
FIG. 2 shows Iso BCFA methyl esters in vernix and meconium (means±SEM, n≤18 newborn) listed left to right in order of molecular weight. i=iso. Key: ☐ vernix; ■ meconium. *p<0.05

As shown in FIG. 2, the vernix iso BCFA profile had odd and even carbon numbered FA from iso-12:0 to iso-16:0, and only even carbon numbers at greater chain lengths. In contrast, meconium iso BCFA was dominated by the shortest chain BCFA in its profile, iso-16:0, which was more than twice the relative concentration of any other BCFA. Five of the eight iso-BCFA appearing in both vernix and meconium were a significantly different proportion of BCFA in the respective profiles; the preponderance of longer chains in meconium lead to significant differences in three of the four iso-BCFA of chain numbers from 20 to 26 carbons.

Example 4

Profile of anteiso BCFA

Figure 3:
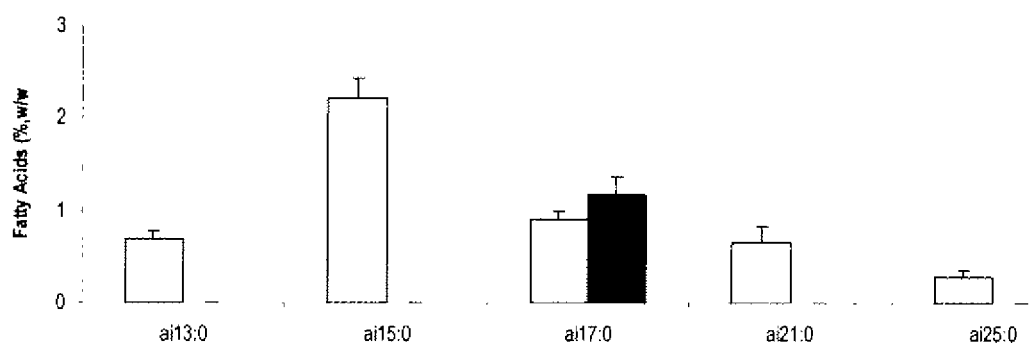
FIG. 3 shows Anteiso BCFA methyl esters in vernix and meconium (means±SEM, n≤18 newborn) listed left to right in order of molecular weight. ai-anteiso. Key: ☐ vernix; ■ meconium. *p<0.05

As shown in FIG. 3, all five anteiso BCFA detected in vernix are odd carbon numbered. They range from 13 to 25 carbons, and only one, anteiso-17:0, is found in meconium.

Example 5

Profile of the Straight Chain, n-FA Profiles for Vernix and Meconium

Figure 4:
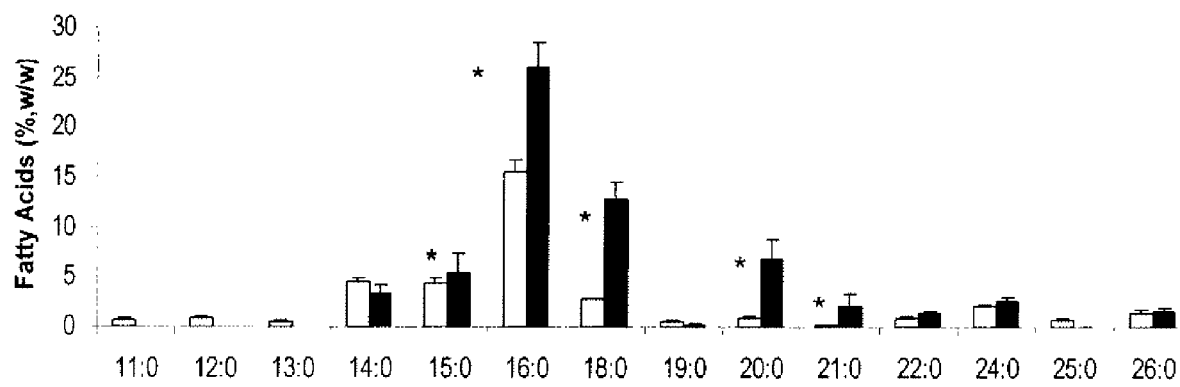
FIG. 4 shows normal (straight chain) FAME in vernix (means±SEM, n≤18 newborn) listed left to right in order of molecular weight. Key: ☐ vernix; ■ meconium. *p<0.05

As shown in FIG. 4, vernix normal FA had 11 to 26 carbon atoms, and meconium FA had 14 to 26 carbons, and both contained small amounts of odd chain number FA. Again, meconium BCFA tended to be of greater molecular weight.

The presence of BCFA in both vernix and meconium of healthy term infants indicates that BCFA are a major component of gut contents of normal term newborns, and their presence in meconium implies that they are present throughout the length of the gut. As such, BCFA are a component of the GI tract milieu present when the first few environmental microorganisms appear in the initial stage of gut colonization during and immediately after parturition or Cesarean section. In meconium, the systematic shift in BCFA profiles to high molecular weights, as well as the absence of most BCFA other than iso-BCFA, indicates that the fetal alimentary canal readily absorbs and metabolizes most BCFA.

There are many reports of BCFA in breastmilk, with the earliest and most extensive, showing 54 BCFA with a cumulative concentration of 1.5% w/w (Egge et al., "Minor Constituents of Human Milk. IV. Analysis of the Branched Chain Fatty Acids," *Chem Phys Lipids* 8:42-55 (1972), which is hereby incorporated by reference in its entirety). A 1981 paper measured the concentration of BCFA in mature Australian breast milk to be a total of 0.84% w/w and one BCFA, anteiso-17:0 in colostrum at 0.45% w/w of fatty acids, exceeding the concentrations of DHA (0.32% w/w) and ARA (0.40% w/w) in the same mother's mature breastmilk (Gibson et al., "Fatty Acid Composition of Human Colostrum and Mature Breast Milk," *Am J Clin Nutr* 34:252-257 (1981), which is hereby incorporated by reference in its entirety). Chen reported four BCFA with a cumulative concentration of 0.58%, w/w in Canadian breastmilk (Chen et al., "Trans Fatty Acid Isomers in Canadian Human Milk," *Lipids* 30:15-21 (1995), which is hereby incorporated by reference in its entirety. A study of California women yielded an average of 0.60% BCFA for the four BCFA that were reported (15:0, 16:0, 17:0, 18:0, branch location not reported) (Aitchison et al., "Influence of Diet on Trans Fatty Acids in Human Milk,"

*Am J Clin Nutr* 30:2006-2015 (1977), which is hereby incorporated by reference in its entirety). Corso found six BCFA in the milk of 40 women in southern Italy (Corso et al., "Gaschromatography-mass Spectrometry Analysis of Fatty Acids in Human Milk from Forty Puerperae Living in Southern Italy," *Riv Eur Sci Med Farmacol* 17:215-219 (1995), which is hereby incorporated by reference in its entirety), with anteiso-17:0 ranging from 0.12 to 0.93% of total fatty acids. This variability is not unlike that for DHA; breastmilk DHA ranges between 0.06% w/w and 1.40% w/w (Brenna et al., "Docosahexaenoic and Arachidonic Acid Concentrations in Human Breast Milk Worldwide," *Am J Clin Nutr* 85:1457-1464 (2007), which is hereby incorporated by reference in its entirety). Many, but not all, breastmilk fatty acid concentrations are closely linked to the dietary intake of the fatty acid or its precursor, including DHA to which the wide reported range is ascribed (Brenna et al., "Docosahexaenoic and Arachidonic Acid Concentrations in Human Breast Milk Worldwide," *Am J Clin Nutr* 85:1457-1464 (2007), which is hereby incorporated by reference in its entirety). It is most likely that the absence of BCFA identification in most breast milk FA papers is due to their low concentration, their appearance in a GC trace amidst the major saturates and monounsaturates in the chromatogram, and the historical absence of a compelling metabolic role for them.

The exposure of the gut to BCFA in utero, and possibly from breastmilk, is greater than any other period of life, because BCFA are at trace levels in normal foods. The unique niche represented by BCFA and other components in the human gut may be important for establishing commensal bacteria during colonization. BCFA are prominent membrane components of many bacterial species (Kaneda et al., "Iso- and Anteiso-Fatty Acids in Bacteria: Biosynthesis, Function, and Taxonomic Significance," *Microbiol Rev* 55:288-302 (1991) and Huang et al., "Basic Characteristics of *Sporolactobacillus inulinus* BCRC 14647 for Potential Probiotic Properties," *Curr Microbiol* 54:396-404 (2007), which are hereby incorporated by reference in their entirety). For instance, BCFA constitute 95% of the FA in several bacilli and *lactobacilli*, including *Sporolactobacillus inulinus*, which has very recently been shown to be a probiotic candidate (Huang et al., "Basic Characteristics of *Sporolactobacillus inulinus* BCRC 14647 for Potential Probiotic Properties," *Curr Microbiol* 54:396-404 (2007), which is hereby incorporated by reference in its entirety). The FA of nine *Bifidobacterium* strains include BCFA such as iso-14:0, anteiso-15:0, iso-16:0 and iso-18:0 at various levels (0.6-24.6% w/w). iso-14:0 is the second most abundant FA in *Bifidobacterium breve* with levels as high as 24.6% w/w (Veerkamp et al., "Fatty Acid Composition of *Bifidobacterium* and *Lactobacillus* Strains," *J Bacterial* 108:861-867 (1971), which is hereby incorporated by reference in its entirety). It is reasonable to hypothesize that the presence of BCFA in the neonatal gut would alter the mix of dominant species, favoring those organisms that use BCFA in their membranes, and it is postulated that BCFA are a unique feature of the human fetal gut favoring the growth of commensal bacteria during colonization.

This hypothesis has implications for colonization of the GI tract of very premature infants, and may be a factor in the development of necrotizing enterocolitis (NEC), the etiology and pathogenesis of which is not well understood (Caplan et al., "Bifidobacterial Supplementation Reduces the Incidence of Necrotizing Enterocolitis in a Neonatal rat Model," *Gastroenterology* 117:577-583 (1999) and Claud et al., "Hypothesis: Inappropriate Colonization of the Premature Intestine Can Cause Neonatal Necrotizing Enterocolitis," *Faseb J* 15:1398-1403 (2001), which are hereby incorporated by reference in their entirety). NEC is one of the major causes of morbidity in premature infants (Caplan et al., "Bifidobacterial Supplementation Reduces the Incidence of Necrotizing Enterocolitis in a Neonatal rat Model," *Gastroenterology* 117:577-583 (1999), which is hereby incorporated by reference in its entirety) though it is certainly related to pathogen overgrowth (Hallstrom et al., "Effects of Mode of Delivery and Necrotising Enterocolitis on the Intestinal Microflora in Preterm Infants," *Eur J Clin Microbial Infect Dis* 23:463-470 (2004), which is hereby incorporated by reference in its entirety). Leading hypotheses with empirical support are that NEC is related to prematurity, enteral feeding, and bacterial colonization (Claud et al., "Hypothesis: Inappropriate Colonization of the Premature Intestine Can Cause Neonatal Necrotizing Enterocolitis," *Faseb J* 15:1398-1403 (2001), which is hereby incorporated by reference in its entirety). Importantly, it has not been observed prenatally. NEC risk is higher among lower gestational age infants and is rare in term infants (Beeby et al., "Risk Factors for Necrotising Enterocolitis: the Influence of Gestational Age," *Arch Dis Child* 67:432-435 (1992), which is hereby incorporated by reference in its entirety). Breast milk consumption is associated with a lower incidence of NEC (Claud et al., "Hypothesis: Inappropriate Colonization of the Premature Intestine Can Cause Neonatal Necrotizing Enterocolitis," *Faseb J* 15:1398-1403 (2001) and Lucas et al., "Breast Milk and Neonatal Necrotising Enterocolitis," *Lancet* 336:1519-1523 (1990), which are hereby incorporated by reference in their entirety). Although no specific pathogenic bacteria has been associated with NEC (Lucas et al., "Breast Milk and Neonatal Necrotising Enterocolitis," *Lancet* 336:1519-1523 (1990), which is hereby incorporated by reference in its entirety), supplementation of premature animals and infants with probiotic strains appear to reduce its incidence (Caplan et al., "Bifidobacterial Supplementation Reduces the Incidence of Necrotizing Enterocolitis in a Neonatal rat Model," *Gastroenterology* 117:577-583 (1999) and Hoyos et al., "Reduced Incidence of Necrotizing Enterocolitis Associated with Enteral Administration of *Lactobacillus acidophilus* and *Bifidobacterium infantis* to Neonates in an Intensive Care Unit," *Int J Infect Dis* 3:197-202 (1999), which are hereby incorporated by reference in their entirety). With these considerations, it is hypothesized that BCFA have a role in enhancing proper GI colonization: vernix begins to appear around week 24 of gestation and accumulates as particulates in amniotic fluid toward term (Narendran et al., "Interaction between Pulmonary Surfactant and Vernix: A Potential Mechanism for Induction of Amniotic Fluid Turbidity," *Pediatr Res* 48:120-124 (2000), which is hereby incorporated by reference in its entirety), thus, the GI tract of very premature infants is not exposed to vernix BCFA prenatally. Postnatally they would be exposed to BCFA if breastfed, but formula-fed preterms would not be exposed to BCFA since they are not a component of preterm formulas. Finally, it is noted that the incidence of NEC drops as gestational age approaches normal term. Therefore later term premature infants would be exposed to some BCFA and may benefit if the hypothesis is correct.

The mass of BCFA entering and exiting the alimentary canal can be estimated. At term, amniotic fluid lipids are about 154 mg/L (Biezenski et al., "Studies on the Origin of Amniotic Fluid Lipids I. Normal Composition," *Am J Obstet Gynecol* 102:853-861 (1968), which is hereby incorporated by reference in its entirety), of which about 52 mg/L are phospholipids that are likely to originate as BCFA-free lung surfactant (Narendran et al., "Interaction between Pulmonary Surfactant and Vernix: A Potential Mechanism for Induction of Amniotic Fluid Turbidity," *Pediatr Res* 48:120-124 (2000)

and Rissmann et al., "New Insights into Ultrastructure, Lipid Composition and Organization of Vernix Caseosa," *J Invest Dermatol* 126:1823-1833 (2006), which are hereby incorporated by reference in their entirety). Thus, the amniotic fluid vernix FA concentration is about 102 mg/L. Of this, the measurements indicate that 57% are FA, to yield 58 mg/L. The data (Table 2) further indicate that 29% are BCFA, to yield 17 mg/L BCFA. The fetus is estimated to swallow 200 to 500 ml/day of amniotic fluid near term (Pritchard et al., "Deglutition by Normal and Anencephalic Fetuses," *Obstet Gynecol* 25:289-297 (1965) and Pritchard et al., "Fetal Swallowing and Amniotic Fluid Volume," *Obstet Gynecol* 28:606-610 (1966), which are hereby incorporated by reference in their entirety), and taking the midpoint of this range, 350 ml/day, 6 mg BCFA per day enter the fetal GI tract amounting to 30×6=180 mg BCFA in the last month of gestation. Meconium is the output of the GI tract integrated from about 12 weeks gestation. Total meconium for 27 term infants was reported (Friel et al., "Trace Elements in Meconium from Preterm and Full-term Infants," *Biol Neonate* 55:214-217 (1989), which is hereby incorporated by reference in its entirety), to be 8.9 g wet weight, averaging 32% dry weight, or 2.8 g. The data indicate that about 0.55% is BCFA, or about 16 mg average total BCFA in meconium. This value is an order of magnitude lower than the estimate of the BCFA swallowed in the last month of gestation, and suggests that most of the BCFA disappear during transit. The distribution and structural characteristics of BCFA that do appear in meconium reflect processing of vernix by the enterocytes. The present invention shows that C11-15 BCFA, as well as nearly all BCFA apart from iso-BCFA, are absent from meconium and thus must have been metabolized. The nature of this metabolism remains to be determined, in part because BCFA and their interaction with human enterocytes has not been studied.

Chain elongation is one likely metabolic transformation that would explain the absence of C11-15 BCFA, and preponderance of longer chain BCFA, in meconium. Suggestive evidence in support of this hypothesis is found in the data of FIG. 1. The significantly greater level of meconium iso-16:0 compared to vernix iso-16:0, is roughly the sum of vernix iso-14:0 and iso-16:0, consistent with the hypothesis that elongation of vernix iso-14:0 adds to the existing iso-16:0. Similar observations apply to meconium iso-20:0 and vernix iso-18:0 and iso-20:0.

Medium chain fatty acids (C8-C14) are commonly fed to premature infants, because they are efficiently absorbed through the gastric mucosa, directly transported to the liver via the portal vein, and oxidized by the immature GI tract. Although the BCFA with 15 or fewer carbons are absent from meconium, FIG. 4 shows that the FA n-14:0 and n-15:0 are partially excreted. This observation implies that there is selective uptake and retention of BCFA by the fetal GI tract that may not operate as efficiently for the n-FA.

The present measurements of BCFA are in line with previous data. BCFA constituted almost one third of all FA in vernix (Kaerkkaeinen et al., "Lipids of Vernix Caseosa," *J Invest Dermatol* 44:333-338 (1965) and Nicolaides et al., "The Structures of the Branched Fatty Acids in the Wax Esters of Vernix Caseosa Lipid," *Lipids* 11:781-790 (1976), which are hereby incorporated by reference in their entirety), and the levels of vernix SFA, MUFA and PUFA were within the range encompassed by previous reports (Rissmann et al., "New Insights into Ultrastructure, Lipid Composition and Organization of Vernix Caseosa," *J Invest Dermatol* 126:1823-1833 (2006); Nicolaides et al., "Further Studies of the Saturated Methyl Branched Fatty Acids of Vernix Caseosa Lipid," *Lipids* 11:781-790 (1976); and Nicolaides et al., "The Structures of the Branched Fatty Acids in the Wax Esters of Vernix Caseosa Lipid," *Lipids* 11: 901-905 (1971), which are hereby incorporated by reference in their entirety). Only odd numbered carbon anteiso BCFA were found, consistent with some previous reports (Nicolaides et al., "Further Studies of the Saturated Methyl Branched Fatty Acids of Vernix Caseosa Lipid," *Lipids* 11:781-90 (1976); Nicolaides et al., "The Structures of the Branched Fatty Acids in the Wax Esters of Vernix Caseosa," *Lipids* 6:901-905 (1971) and Haahti et al., "Fatty Acids of Vernix Caseosa," *Scand J Clin Lab Invest* 13:70-73 (1961), which are hereby incorporated by reference in their entirety), but not with others (Rissmann et al., "New Insights into Ultrastructure, Lipid Composition and Organization of Vernix Caseosa," *J Invest Dermatol* 126:1823-1833 (2006) and Kaerkkaeinen et al., "Lipids of Vernix Caseosa," *J Invest Dermatol* 44:333-338 (1965), which are hereby incorporated by reference in their entirety). BCFA averaged 17% w/w of all FA in meconium in the samples. The single previous study showing BCFA in meconium reported only on the free fatty acid fraction and used GC with retention time matching for identification. iso FA with 22 and 24 carbons were identified at 4% w/w and 6% w/w respectively, and nine other iso-BCFA were tentatively assigned (C14-21, 25) with no percent fraction provided.

Though five anteiso BCFA were detected in vernix, anteiso-17:0 was the sole anteiso BCFA detected in meconium, and there is no obvious explanation as to why this was the case. Weanling rats fed 100 mg/week anteiso-17:0 in an otherwise fat free diet excreted 8-10% in the feces and stored a similar amount in adipose tissue (Livingston et al., "The Metabolism in the Rat of Naturally Occurring (+)-14-Methylhexadecanoic Acid," *Biochem J* 65:438-440 (1957) which is hereby incorporated by reference in its entirety), and apparently also converted a small amount anteiso-15:0. The remaining 80% was metabolized to substances other than anteiso FA. The levels of anteiso-17:0 have been reported to be the highest among all BCFA in at least one study of breastmilk (Gibson et al., "Fatty Acid Composition of Human Colostrum and Mature Breast Milk," *Am J Clin Nutr* 34:252-257 (1981), which is hereby incorporated by reference in its entirety), and it is notable that anteiso-17:0 is a major lipids constituent of many bacterial membrane (Kaneda et al., "Iso- and Anteiso-Fatty Acids in Bacteria: Biosynthesis, Function, and Taxonomic Significance," *Microbiol Rev* 55:288-302 (1991), which is hereby incorporated by reference in its entirety).

The combined levels of the middle chain monomethyl and dimethyl BCFA in the vernix samples were similar to the levels reported in a single vernix sample by Nicolaides & Apon (Nicolaides et al., "The Structures of the Branched Fatty Acids in the Wax Esters of Vernix Caseosa Lipid," *Lipids* 11:781-790 (1976), which is hereby incorporated by reference in its entirety). In the sample of 18 newborns, the average proportions of dimethyl monomethyl BCFA dominated over middle chain monomethyl BCFA. The first methyl branch in the dimethyl BCFA was located predominantly on the fourth carbon of the chain, consistent with previous findings (Nicolaides et al., "The Structures of the Branched Fatty Acids in the Wax Esters of Vernix Caseosa Lipid," *Lipids* 11:781-790 (1976) and Nicolaides et al., "The Structures of the Branched Fatty Acids in the Wax Esters of Vernix Caseosa," *Lipids* 6:901-905 (1971), which are hereby incorporated by reference in its entirety). However, in the present invention, the second methyl branch in half of the dimethyl BCFA was located on an odd numbered carbon, and in almost all the dimethyl BCFA, this methyl branch was located on the anteiso carbon of the FA chain.

In summary, there are dramatic and systematic differences in BCFA composition between vernix and meconium, indicating that BCFA are actively metabolized in the fetal GI tract. This observation implies that vernix should be considered a nutritional agent, and that BCFA are a normal and quantitatively substantial component of the normal term newborn GI tract. Further studies are warranted to understand the uptake and metabolism of BCFA by enterocytes, and the role of BCFA during bacterial colonization. The absence of vernix, and BCFA, in the GI tract of very premature, formula-fed infants may have a role in the etiology of NEC, among the most devastating conditions facing the preterm infant.

Materials and Methods for Examples 6-7

Caco-2 Cells

Caco-2 cells are a human colon cancer cell line which was introduced in the 1980s as a model for enterocyte metabolism and rapidly became a standard in vitro model for studies of absorption and metabolism in enterocytes. The cells are often cultured on microporous membranes where they assume a polarized configuration, with villi developing on the apical side and secretion of chylomicrons and very low density lipoproteins on the basolateral side (Traber et al., "Polarized Secretion of Newly Synthesized Lipoproteins by the Caco-2 Human Intestinal Cell Line," *J Lipid Res* 28:1350-63 (1987) and Luchoomun et al., "Assembly and Secretion of Chylomicrons by Differentiated Caco-2 Cells. Nascent Triglycerides and Preformed Phospholipids are Preferentially Used for Lipoprotein Assembly," *J Biol Chem* 274:19565-72 (1999), which are hereby incorporated by reference in their entirety). Among the limitations of in vitro systems is their metabolic similarity to the in vivo condition. Caco-2 cells differentiate and make microvilli resembling those of the upper intestine, however they are not as dense as the in vivo condition, and are considered similar to fetal cells (Blais et al., "Common Characteristics for Na+-dependent Sugar Transport in Caco-2 Cells and Human Fetal Colon," *J Membr Biol* 99:113-25 (1987) and Zweibaum et al., "Sucrase-isomaltase: A Marker of Foetal and Malignant Epithelial Cells of the Human Colon," *Int J Cancer* 32:407-12 (1983), which are hereby incorporated by reference in their entirety). Moreover, the normal contents of the fetal and neonatal GI tract are much less varied than the contents of the adult GI tract. The fetal gut processes amniotic fluid while the neonatal GI tract processes breast milk or its substitutes. The adult must process any conceivable food, a complication that requires careful design of simulated digestive model systems prior to study of food absorption by Caco-2 (Fairweather-Tait et al., "The Usefulness of In Vitro Models to Predict the Bioavailability of Iron and Zinc: A Consensus Statement from the HarvestPlus Expert Consultation," *Int J Vitam Nutr Res* 75:371-4 (2005), which is hereby incorporated by reference in its entirety).

These considerations suggest that Caco-2 cells are most appropriate for modeling the present invention. Apart from limitations in extrapolating results of Caco-2 data to the in vivo situation, experts considering BCFA as nutritional or therapeutic agent will wish to have data on absorption and metabolism in Caco-2 cells as reference data, thereby justifying the use of the model.

Caco-2 cells were grown to confluence on a solid bottom, multi-well plates in DMEM (Dulbecco's Modified Eagle's Medium) containing 10% v:v fetal bovine serum. Twenty-four hours prior to treatment with BCFA, DMEM was replaced with MEM (Minimum Essential Medium). Two wells were incubated with 1.2 mmol each of a mixture of four, pure BCFA (iso-14:0, anteiso-17:0, iso-18:0, iso-20:0) as free fatty acids (FFA) obtained from Larodan Lipids (Malmo, Sweden). Two others served as controls. Cells were incubated for 18 hours, after which media was removed and the cells were thoroughly and carefully washed three times. Cell lipids were extracted and FAME prepared for GC/MS.

Example 6

Figure 5:
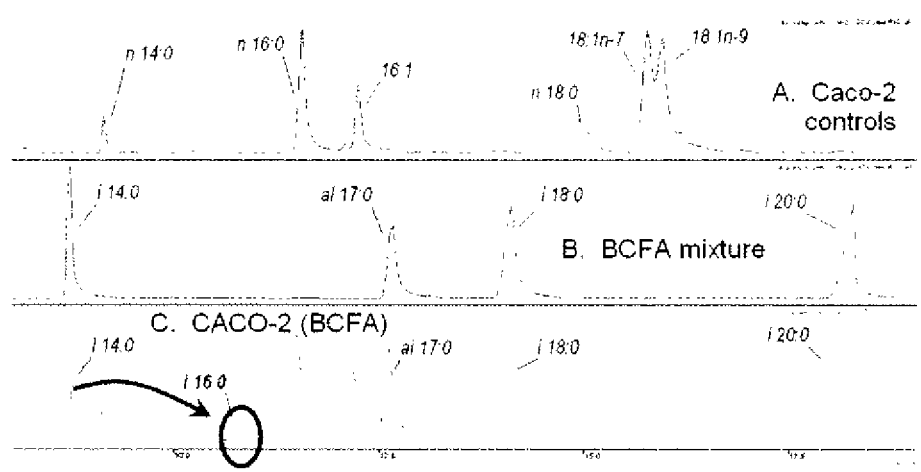
FIG. 5A-C shows GC/MS reconstructed ion chromatograms (RIC) from Caco-2 BCFA uptake experiment. RIC section shows saturated and monounsaturated C14-18 fatty acids.

BCFA Interaction with Caco-2 Cells: Caco-2 Cells Readily Take Up BCFA from Media and Biosynthesize New BCFA from Exogenous BCFA FIG. 5 outlines the GC/MS data, presented as reconstructed ion chromatograms (RIC) of the section of the chromatogram corresponding to the elution time of BCFA. In FIG. 5A, the top panel shows the control cells C14-C18 saturated and monounsaturated FA. There is no evidence of BCFA above 0.1% of fatty acids in these data. In FIG. 5B, the middle panel is a RIC of the BCFA mixture used to treat the cells. In FIG. 5C, the bottom panel is the RIC of the Caco-2 cells incubated for 18 hours with BCFA. Careful inspection of the three panels reveals that the RIC of panel (FIG. 5C) appears very much like a composite of the chromatograms in (FIG. 5A) and (FIG. 5B). The cells have taken up a large amount of BCFA, such that they are now the dominant saturated FA. However, a peak appearing in the treated cells but neither the control cells (FIG. 5A) nor the BCFA mixture (FIG. 5B) is iso-16:0. This BCFA can only have arisen by biosynthesis, likely to be by elongation of iso-14:0. It was calculated that the newly biosynthesized iso-16:0 is about 10% of the iso-14:0 peak, indicating substantial conversion activity over 18 h if all iso-16:0 arises from chain elongation of iso-14:0. In these cells, BCFA constitute 33% of the total FA, and 53% of the saturated FA. This contrasts with 1.7% 20:4 (arachidonic acid) and 0.86% docosahexaenoic acid (DHA), two LCPUFA of considerable metabolic importance, in these cells.

Figure 6:
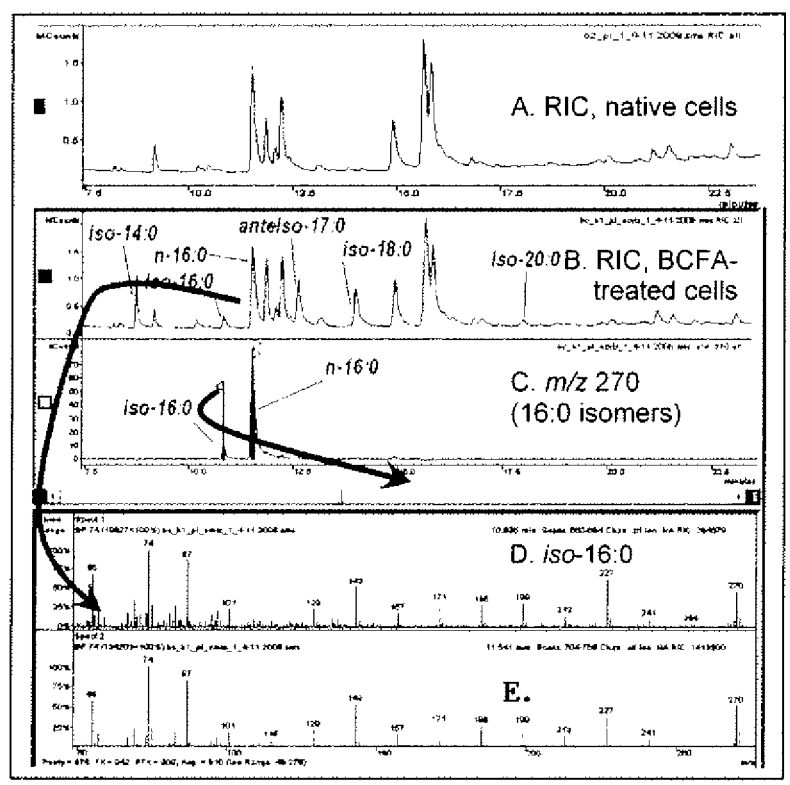
FIG. 6A-E shows phospholipids fatty acids purified from Caco-2 cells treated with BCFA.
Figure 7:
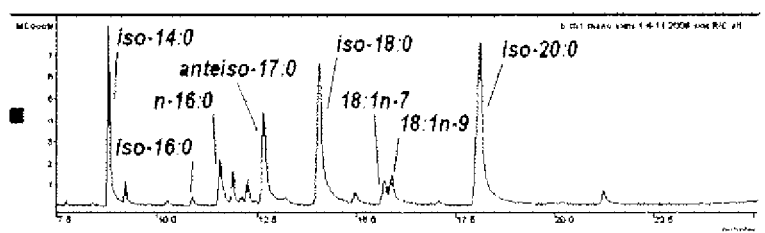
FIG. 7 shows monoacylglycerol (MAG) FA from BCFA-treated Caco-2 cells. The BCFA mixture dominates MAG FA, and they are represented in close proportion to the parent free fatty acid mixture shown in FIG. 5B. Compare iso-20:0 to iso-14:0 peak heights to those of FIG. 6B. Note also that the iso-16:0 to iso-14:0 ratio is small compared to that of FIG. 6B, indicating relatively low biosynthesis of iso-16:0 appearing in this lipid class.

FIGS. 6 and 7 present profiles of BCFA within phospholipids (PL) and monoacylglycerols (MAG) of the same BCFA-treated cells shown in FIG. 5. FIG. 6 shows that BCFA are incorporated into PL at about half the level of endogenous FA (compare heights of, e.g., iso-14:0 vs n-16:0 in FIG. 6B). Note also that the iso-20:0 peak is much smaller compared to other BCFA (compare FIGS. 5A, 5C, 6B, and 7). A selected ion chromatogram and mass spectra are also shown to further illustrate positive identification of the 16:0 isomers as an example.

FIG. 7 shows that BCFA are by far the dominant FA in MAG (compare iso-14:0 vs n-16:0). Newly synthesized iso-16:0 is very low compared to iso-14:0 in this fraction. It is likely that free BCFA entering the cells are initially incorporated into MAG and thus the concentration is highest, and relative appearance of newly synthesized iso-16:0 is low.

Example 7

Figure 8:
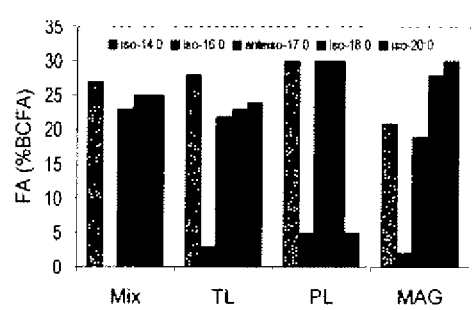
FIG. 8 shows BCFA profiles in a parent free fatty acid mixture and in lipids of BCFA-treated Caco-2 cells. Iso-16:0 is present in all cell extracts. Note especially the selection against iso-20:0 in PL, and favoring iso-20:0 in MAG.

Caco-2 Cells Selectively Incorporate BCFA into Lipid Classes Based on Chain Length and on Lipid Class FIG. 8 is a summary of the BCFA profiles in each sample, showing that the initial FFA mix was transformed into PL and MAG, with chain length selectivities that could help explain the vernix/meconium BCFA profiles.

A mixture of BCFA was used to generate this preliminary data so to provide a basic simulation of vernix BCFA without protein or other confounding compounds. Cells are treated with individual BCFA, anteiso-17:0, iso-18:0, and others, to establish whether iso-14:0 is elongated or iso-18:0 is chain shortened to yield iso-16:0, for instance.

The data in the present invention is consistent with the hypothesis's prediction that the difference in distribution between vernix and meconium BCFA arises, at least in part, due to uptake and differential metabolism of BCFA. These are among the rare data on BCFA metabolism in mammals apart from studies in skin and surface glands.

BCFA are a major component of the normal term infant alimentary canal. The present invention will develop the knowledge on BCFA metabolism in intestinal cells, focused on the practical issue of NEC, which develops in immature infants with negligible or low gut BCFA (simulated by control cells).

Example 8

Anaerobic Cultures and Vernix

Anaerobic microbial growth studies were performed, and whether vernix influences proliferation of commensal or pathogenic bacteria was examined. Two commensal bacteria (Bifidobacteria *breve* and *S. inulinus*) and three pathogens (*C perfringens, C difficile*, both obligate anaerobes, and *E coli*, a facultative anaerobe) were grown anaerobically in pure culture. Two nutrient media were used (Trypticase Soy Broth and Nutrient Broth ("NB", Difco)). Vernix leftover from that used to generate data above was dissolved in ethanol, autoclaved, and added to cultures (Vernix). Ethanol alone was used as a control (C).

FIG. 9 shows that *B. breve* vernix developed optical density 80% faster than the controls. The growth enhancement in *S. inulinus* was dramatic in both media. In contrast, the pathogens in the right panels are not different between vernix and the controls.

The present invention provides preliminary evidence that vernix itself influences gut flora. Upon reflection, it makes sense that friendly bacterial growth is enhanced by vernix, the normal contents of the term newborn human gut, and that vernix should put opportunistic pathogens at no special advantage.

It cannot be confirmed from the present invention that it was the BCFA component of vernix that enhanced growth. However, it is likely that the bioactivity of vernix peptides are substantially impaired or inactivated after dissolution in ethanol and autoclaving, while the activities of saturated lipids are not affected. Second, the magnitude of growth by each bacteria is not an indicator of its competitive fitness; one cannot conclude that *C. perfringens* is the most fit organism because of its fast growth characteristics in this medium. These data apply only to the influence of sterilized vernix per se on growth. Properly controlled competitive growth assays are required for this purpose. It is important to note that these are all the data from the first attempt with these cultures. The conditions have not yet been optimized. For instance, a new paper shows that bile enhances uptake of BCFA by the bifidobacteria (Ruiz et al., "Cell Envelope Changes in *Bifidobacterium animalis* ssp. *lactis* as a Response to Bile," *FEMS Microbiol Lett* 274:316-22 (2007), which is hereby incorporated by reference in its entirety), and continuing studies will take this into account.

The dose of BCFA was 23 µg per 20 ml culture, or about 1 µg/ml, based on addition of 380 µg vernix (dry weight). This can be compared to the infant's estimated exposure. Vernix particles that are relatively dilute in gulped amniotic fluid will be rapidly concentrated in the newborn gut as water and electrolytes are absorbed. Amniotic fluid contains 138 µg lipids/ml between 34-40 weeks gestation, and >39 weeks it contains 386 µg lipids/ml (Lentner C., *Geigy Scientific Tables*, 8th ed. New Jersey: Ciba-Geigy, (1981), which is hereby incorporated by reference in its entirety), most of which are vernix, with surfactant and other minor lipids present. This concentration rises dramatically upon absorption of water and conversion of the liquid amniotic fluid into a paste in the upper infant gut. Based on the measurements of the concentration of BCFA in vernix (6% dry weight) and meconium (0.5% dry wt), a total concentration of 1 mg BCFA/ml meconium can be estimated. Based on this analysis, microorganisms arriving in the gut after birth will therefore encounter much higher concentrations of BCFA, though it cannot be said if they will behave similarly to BCFA dissolved in ethanol. Nevertheless, the present invention shows that low levels of vernix components, compared to the gut environment, may exert major effects.

It is noted that the newest (preliminary) data are consistent with the hypothesis that vernix enhances the growth of commensal organisms, leaving opportunistic pathogen growth unaffected. There is evidence, however, that vernix lipids per se have antimicrobial properties, and interact synergistically with an antimicrobial vernix peptide to inhibit growth of at least one model organism. Vernix lipids inhibited the growth of *Bacillus megaterium* compared to a no lipid control. Moreover, the addition of vernix peptide LL-37, when mixed in a ratio of 3:1 with vernix lipids, results in further growth inhibition (Tollin et al., "Vernix Caseosa as a Multi-component Defence System Based on Polypeptides, Lipids and Their Interactions," *Cell Mol Life Sci* 62:2390-9 (2005), which is hereby incorporated by reference in its entirety). Importantly, that study detected 23% "unidentified fatty acids" among their vernix fatty acids, which can safely be assumed to be overwhelmingly BCFA.

Importantly, the proposed studies, including competition experiments, naturally evaluate the relative pro-commensal, anti-pathogen ("antimicrobial") properties of vernix and its lipids when focused upon the hypothesis, as cast.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a gastrointestinal condition in a subject, said method comprising: selecting a subject in need of treatment of the gastrointestinal condition, and administering a composition comprising one or more branched chain fatty acids to the subject under conditions effective to treat the gastrointestinal condition in the subject, wherein the one or more branched fatty acids is a $C_{11}$ to $C_{26}$ alkyl substituted branched chain fatty acid or mixtures thereof, wherein the composition comprises at least 2 wt % of the one or more branched chain fatty acids, wherein the gastrointestinal condition is associated with inflammation, and wherein the composition is not milk or colostrum.

2. The method of claim 1, wherein the gastrointestinal condition is mediated by infection of the subject's gastrointestinal tract by a pathogenic bacteria.

3. The method of claim 1, wherein the gastrointestinal condition is necrotizing enterocolitis.

4. The method of claim 1, wherein the gastrointestinal condition is a disease of the intestine involving inflammation.

5. The method of claim 4, wherein the gastrointestinal condition is inflammatory bowel disease.

6. The method of claim 1, wherein the one or more branched chain fatty acid is selected from the group consisting of 4,7-dimethyl-nonanoic acid, 4,8-dimethyl-decanoic acid, 8-methyl-undecanoic acid, iso-dodecanoic acid, 4,8-dimethyl-undecanoic acid, 4,9-dimethyl-undecanoic acid, iso-tridecanoic acid, anteiso-tridecanoic acid, 4,10-dimethyl-dodecanoic acid, iso-tetradecanoic acid, 4,11-dimethyl-tridecanoic acid, iso-pentadecanoic acid, anteiso-pentadecanoic acid, 8,10-dimethyl-tetradecanoic acid, 4,12-dimethyl-tetradecanoic acid, iso-hexadecanoic acid, 2-methyl hexadecanoic acid, 4,11-dimethyl-pentadecanoic acid, 4,13-dimethyl-pentadecanoic acid, iso-heptadecanoic acid, anteiso heptadecanoic acid, iso-octadecanoic acid, iso-eicosanoic acid, anteiso-heneicosanoic acid, iso-dodecanoic acid, iso-tetracosanoic acid, iso-pentacosanoic acid, anteiso-pentacosanoic acid, iso-hexacosanoic acid, phytanic acid, pristanic acid, and mixtures thereof.

7. The method of claim 6, wherein the one or more branched chain fatty acid is selected from the group consisting of iso-hexadecanoic acid, anteiso-hexadecanoic acid, 4,13-dimethylpentadecanoic acid, phytanic acid, pristanic acid, and mixtures thereof.

8. The method of claim 1, wherein the one or more branched chain fatty acid is selected from the group consisting of saturated and monounsaturated fatty acids and mixtures thereof.

9. The method of claim 8, wherein the one or more branched chain fatty acid is a branched form of a fatty acid selected from the group consisting of an octanoic acid, a decanoic acid, a lauric acid, a myristic acid, a palmitic acid, a stearic acid, an eicosanoic acid, a palmitoleic acid, an oleic acid, and mixtures thereof.

10. The method of claim 1, wherein the subject is human.

11. The method of claim 10, wherein the subject is an infant.

12. The method of claim 11, wherein the subject is a newborn infant.

13. The method of claim 10, wherein the subject is a child.

14. The method of claim 10, wherein the subject is an adult.

15. The method of claim 1, wherein the composition comprises at least 25 wt % of the one or more branched chain fatty acids.

16. The method of claim 1, wherein the composition comprises at least 20 wt % of the one or more branched chain fatty acids.

17. The method of claim 1, wherein the composition comprises at least 10 wt % of the one or more branched chain fatty acids.

18. The method of claim 1, wherein the composition comprises at least 5 wt % of the one or more branched chain fatty acids.

19. The method of claim 1, wherein the composition is in the form of a tablet, capsule, powder, solution, suspension, or emulsion.

20. The method of claim 1, wherein the composition is in the form of an emulsion.

21. The method of claim 1, wherein the composition comprises the one or more branched chain fatty acids emulsified in an aqueous phase.

22. The method of claim 1, wherein the composition is a food product supplemented with the one or more branched chain fatty acid.

23. The method of claim 22, wherein the food product is selected from the group consisting of milk, infant formula, baby food, a dietary supplement, vegetable oil, mayonnaise, yogurt, margarine, shortening, and a combination thereof.

24. The method of claim 22, wherein the food product is infant formula.

25. A method of treatment or prevention of necrotizing enterocolitis in a subject, said method comprising: selecting a subject in need of prevention or treatment of necrotizing enterocolitis, and administering a composition comprising one or more branched chain fatty acids to the subject under conditions effective to prevent or treat the necrotizing enterocolitis in the subject, wherein the one or more branched chain fatty acid is a $C_{11}$ to $C_{26}$ alkyl-substituted branched chain fatty acid or mixtures thereof, wherein the composition comprises at least 2 wt % of the one or more branched chain fatty acids and wherein the composition is not milk or colostrum.

26. A method of preventing a gastrointestinal condition in a subject, said method comprising: selecting a subject in need of prevention of the gastrointestinal condition, and administering a composition comprising one or more branched chain fatty acids to the subject under conditions effective to prevent the gastrointestinal condition in the subject, wherein the one or more branched chain fatty acid is a $C_{11}$ to $C_{26}$ alkyl-substituted branched chain fatty acid or mixtures thereof, wherein the composition comprises at least 2 wt % of the one or more branched chain fatty acids, wherein the gastrointestinal condition is necrotizing enterocolitis or inflammatory bowel disease, and wherein the composition is not milk or colostrum.

27. The method of claim 26, wherein the gastrointestinal condition is necrotizing enterocolitis.

28. The method of claim 26, wherein the gastrointestinal condition is inflammatory bowel disease.

29. The method of claim 28, wherein the inflammatory bowel disease is Crohn's disease.

30. The method of claim 26, wherein the one or more branched chain fatty acid is selected from the group consisting of 4,7-dimethyl-nonanoic acid, 4,8-dimethyl-decanoic acid, 8-methyl-undecanoic acid, iso-dodecanoic acid, 4,8-dimethyl-undecanoic acid, 4,9-dimethyl-undecanoic acid, iso-tridecanoic acid, anteiso-tridecanoic acid, 4,10-dimethyl-dodecanoic acid, iso-tetradecanoic acid, 4,11-dimethyl-tridecanoic acid, iso-pentadecanoic acid, anteiso-pentadecanoic acid, 8,10-dimethyl-tetradecanoic acid, 4,12-dimethyl-tetradecanoic acid, iso-hexadecanoic acid, 2-methyl hexadecanoic acid, 4,11-dimethyl-pentadecanoic acid, 4,13-dimethyl-pentadecanoic acid, iso-heptadecanoic acid, anteiso heptadecanoic acid, iso-octadecanoic acid, iso-eicosanoic acid, anteiso-heneicosanoic acid, iso-dodecanoic acid, iso-tetracosanoic acid, iso-pentacosanoic acid, anteiso-pentacosanoic acid, iso-hexacosanoic acid, phytanic acid, pristanic acid, and mixtures thereof.

31. The method of claim 30, wherein the one or more branched chain fatty acid is selected from the group consisting of iso-hexadecanoic acid, anteiso-hexadecanoic acid, 4,13-dimethylpentadecanoic acid, phytanic acid, pristanic acid, and mixtures thereof.

32. The method of claim 26, wherein the one or more branched chain fatty acid is selected from the group consisting of saturated and monounsaturated fatty acids and mixtures thereof.

33. The method of claim 32, wherein the one or more branched chain fatty acid is a branched form of a fatty acid selected from the group consisting of an octanoic acid, a decanoic acid, a lauric acid, a myristic acid, a palmitic acid, a stearic acid, an eicosanoic acid, a palmitoleic acid, an oleic acid, and mixtures thereof.

34. The method of claim 26, wherein the subject is human.

35. The method of claim 34, wherein the subject is an infant.

36. The method of claim 35, wherein the subject is a newborn infant.

37. The method of claim 34, wherein the subject is a child.

38. The method of claim 34, wherein the subject is an adult.

39. The method of claim 26, wherein the composition comprises at least 25 wt % of the one or more branched chain fatty acids.

40. The method of claim 26, wherein the composition comprises at least 20 wt % of the one or more branched chain fatty acids.

41. The method of claim 26, wherein the composition comprises at least 10 wt % of the one or more branched chain fatty acids.

42. The method of claim 26, wherein the composition comprises at least 5 wt % of the one or more branched chain fatty acids.

43. The method of claim 26, wherein the composition is in the form of a tablet, capsule, powder, solution, suspension, or emulsion.

44. The method of claim 26, wherein the composition is in the form of an emulsion.

45. The method of claim 26, wherein the composition comprises the one or more branched chain fatty acids emulsified in an aqueous phase.

46. The method of claim 26, wherein the composition is a food product supplemented with the one or more branched chain fatty acid.

47. The method of claim 46, wherein the food product is selected from the group consisting of milk, infant formula, baby food, a dietary supplement, vegetable oil, mayonnaise, yogurt, margarine, shortening, and a combination thereof.

48. The method of claim 46, wherein the food product is infant formula.

* * * * *